Feb. 21, 1939. F. H. HOWARD Plant Pat. 314
ROSE
Filed Dec. 29, 1936
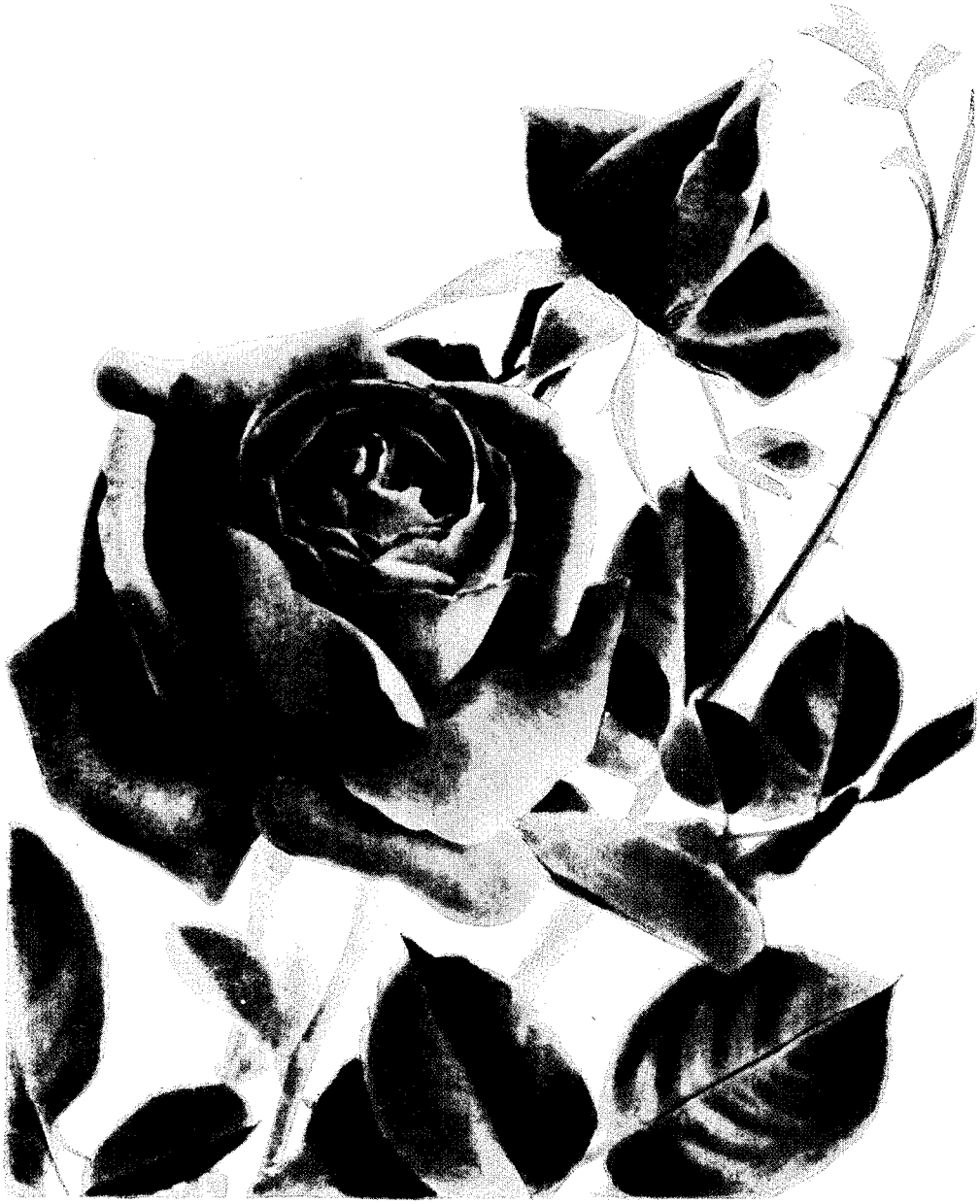
INVENTOR
Frederick Huber Howard
By Orville M. Kile
Plant Patent Agent Patented Feb. 21, 1939

Plant Pat. 314

UNITED STATES PATENT OFFICE

314

ROSE

Frederick Huber Howard, Montebello, Calif.

Application December 29, 1936, Serial No. 118,136

1 Claim. (Cl. 47—61)

My present invention relates to a new and distinct variety of rose plant of the Hybrid Tea class and is a seedling resulting from definite breeding efforts. It is the result of a cross between an unnamed seedling and the variety Rowena Thom. carrying through a series of line bred crosses, with Radiance as one of the progenitors. Asexual reproduction through several seasons has shown the fixity of the distinguishing features. This new variety was developed in an effort to improve red roses in vigor, productiveness and continued brilliancy of color that will not fade or "blue."

The original illustration shows a bud, an open bloom, and foliage of this variety in approximately natural size and color. Following is a more complete description of the plant and flower of this new variety.

*The plant*

Growth habits:
A very strong and vigorous bush rose, attaining a height of three feet or more; a constant and prolific bloomer.

Disease resistance:
Particularly resistant to mildew.

Stems:
Rigid and stiff; light green; very thorny.
*Nodes.*—Heavy; close set; inclined to stagger.

Peduncle:
About 3½ inches in length; smooth; green with a tinge of bronze.

Foliage:
Heavy and abundant.
*Leaves.*—Compound, with three to five leaflets; leathery in texture; nearly round in shape, terminal leaflet averaging 1¾ inches wide by 2 inches long; margin finely serrated.
*Color.*—Bright green on upper surface, reverse lighter.

Rachis:
Flat or only slightly grooved on upper surface; reverse nearly or completely devoid of spines.

Stipules:
Long; slightly reflexed at the joints.

Sepals:
Average moderate length.

*The flower*

Bud:
*Form.*—Conical.
*Color.*—Between Spectrum Red Carmine (Plate I, Ridgway's Color Standards and Nomenclature).
*Opening.*—Opens slowly.

Bloom:
*Form.*—Full and rounded; stamens and pistils not disclosed except in advanced stage of development.
*Size.*—Four and one-half to five and one-half inches in diameter when fully expanded.
*Petalage.*—Double, averaging 35 to 40 petals throughout the year in the inventor's trial plots. Petals are arranged in revolute form, evenly graduated in size. Petals—heavy in texture, with brilliant sheen. Shape—outer petals round with slight point at top. Inner petals nearly round. Behavior—fall cleanly when flower dies. Color—upper surface of petal is of a color not found in Ridgway's Color Standards but is between Spectrum Red (Plate I) and Carmine (Plate I) at certain periods of the season. During the autumn the petals have basal shadings between Oxblood (Plate I) and Maroon (Plate I), with an occasional flake of white in the major exterior series. General color effect—uniform rich crimson-scarlet. There is nothing in Ridgway's Color Standards and Nomenclature like the color of this rose. The nearest would be found between Spectrum Red and Carmine (Plate I). Roses known to me which have coloring nearest like that of this new variety are Gipsy Lass, Hoosier Beauty and Hadley. This comparison to the varieties named relates only to color of flowers. The rose is immune to "blueing" in advanced stages of development.
*Keeping qualities.*—Very pronounced. Blossoms retain their freshness in water for five to six days.
*Fragrance.*—Very fragrant; a fruity tea scent.

*Reproductive organs*

Stamens:
Moderate number.

Filaments:
Moderately varying lengths.

Anthers:
Large size; brownish orange.

Pollen:
Plentiful.

Pistils:
Large; somewhat spreading.

Styles:
White; slightly hirsute.

Stigma:
White with reddish tinge.

Ovaries:
Enclosed in calyx.

Hips:

Large; comparatively smooth; Forest Green (Plate XVII, Ridgway's Color Standards) when immature; drop off before maturity.

Having thus disclosed my invention, what I claim is:

The new and distinct variety of rose plant herein illustrated and described, characterized particularly by its vigor, productiveness, comparative freedom from mildew, and its large blossoms of distinctive coloring, fruity tea fragrance, splendid keeping qualities, and continued brilliancy from early bud stage to fully opened bloom.

FREDERICK HUBER HOWARD.